United States Patent [19]
Wahlberg

[11] Patent Number: 6,003,553
[45] Date of Patent: Dec. 21, 1999

[54] FEMALE LUER CONNECTOR

[75] Inventor: Ulf Harry Wahlberg, Helsingborg, Sweden

[73] Assignee: Becton, Dickinson and Company, Franklin Lakes, N.J.

[21] Appl. No.: 09/101,786

[22] PCT Filed: Nov. 7, 1997

[86] PCT No.: PCT/GB97/03066

§ 371 Date: Nov. 16, 1998

§ 102(e) Date: Nov. 16, 1998

[87] PCT Pub. No.: WO98/23323

PCT Pub. Date: Jun. 4, 1998

[30] Foreign Application Priority Data

Nov. 26, 1996 [GB] United Kingdom .................... 9624532

[51] Int. Cl.⁶ .................................................. F16K 11/085

[52] U.S. Cl. ........................................ 137/625.47; 285/332
[58] Field of Search .......................... 285/9.2, 332, 332.1, 285/334.4; 604/283; 137/625.47

[56] References Cited

U.S. PATENT DOCUMENTS 5,632,735  5/1997  Wyatt et al. .............................. 604/283

*Primary Examiner*—John Fox
*Attorney, Agent, or Firm*—Eric M. Lee

[57] ABSTRACT

A female part of a Luer connector is provided with at least one abutment 10 at or adjacent the distal end of its interior for limiting movement of a mating male part within the female part. The abutment 10 extends around a portion only of the periphery of the interior of the female part thereby minimizing the chances of air traps and allowing the free flow of fluid through the Luer connector.

1 Claim, 1 Drawing Sheet

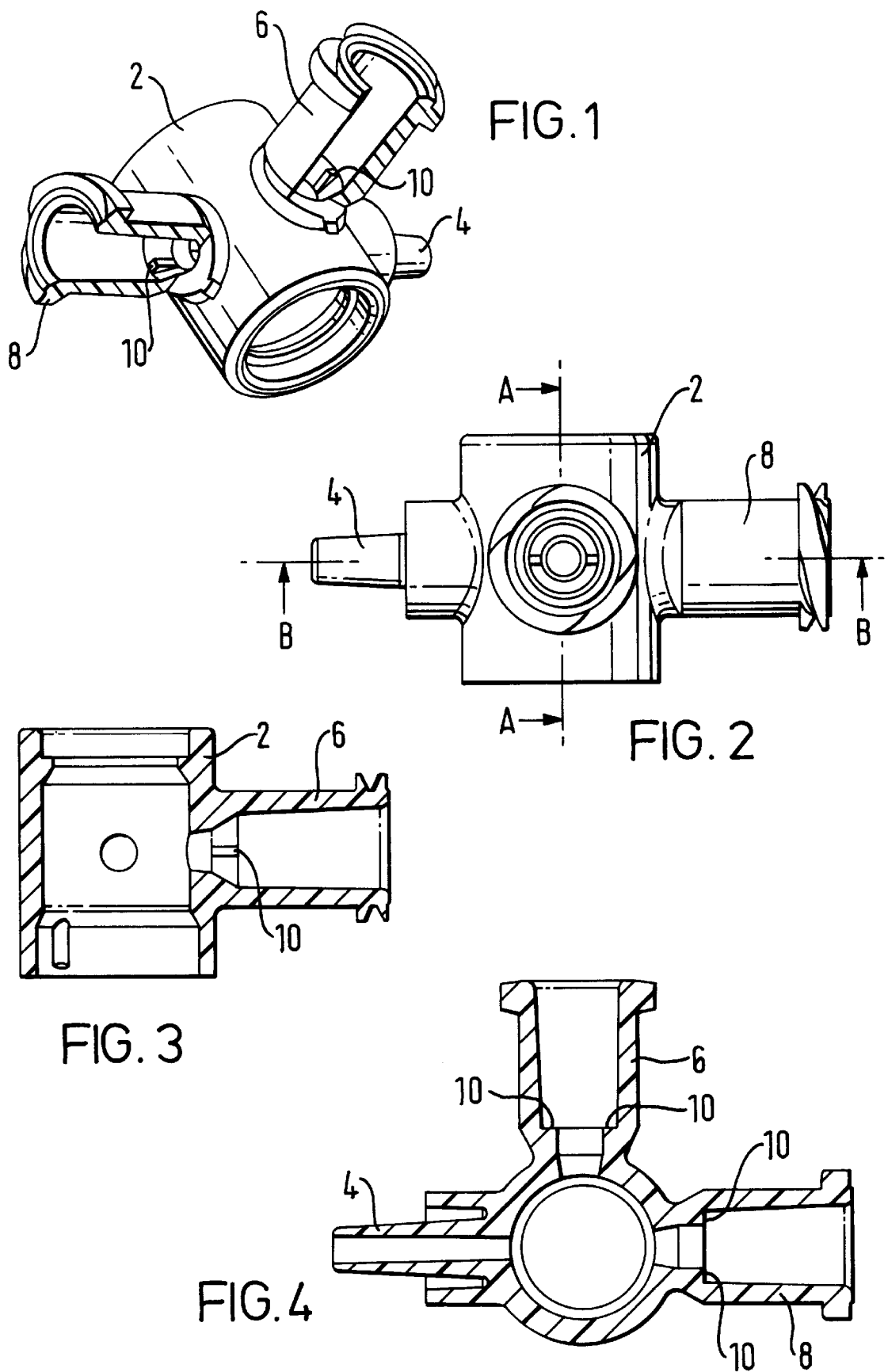

FEMALE LUER CONNECTOR

The present invention relates to Luer connectors.

The International Organisation for Standardisation (ISO) by its International Standard ISO 594 part 1 and part 2 deals with conical fittings with a 6% (Luer) taper for syringes, needles and certain other medical equipment. It covers conical fittings made of rigid and of semi-rigid materials.

Luer connectors are used in particular in medical applications where it is desired to interconnect together male and female connector parts made from plastics material. The interconnecting male and female parts are tapered and so dimensioned according to the Luer standard so that different products from different suppliers will always fit together; the male part being received as a friction fit within the female part or by the lock fitting (ISO 594/2).

An important quality issue for manufacturers and users of plastics Luer connectors is the female part's resistance to external stress. This external stress occurs when a user applies the male part within the female part. Usually the friction between the male and the female part is high so that the stress or tension applied to the female part is limited. However, in situations where the fluid for example is greasy the friction between the parts drops and the stress increases to a very high level. In such conditions, particularly where several different male parts are applied to a female part over a long period of use there is a tendency for the female part to crack with a subsequent leakage of fluid.

It is known from UK Patent 1586744 for an interconnecting male pin and a female box to have mating complementary tapered surfaces; the female box being formed with an inner transversely extending shoulder against which the free end of the male pin abuts.

However, this solution for limiting the movement of a male part within a female part of a Luer connector would have a number of disadvantages. For example, in the situation where the tolerances on the external dimensions of the male part and the internal dimensions of the female part are such that when the male part enters the female part there is a space between the free end of the male part and the shoulder formed in the female part; said space will act as a trap for air when fluid is passed through the Luer connector. Such a space or trap will also adversely affect the smooth flow of fluid passing through the Luer connector.

Again, guide-wires are sometimes passed through Luer connectors which have a configuration at their free leading end of a J-shape. It has been known for the space or trap to allow the end of the guide-wire to snag against the shoulder.

It is an aim of the present invention to modify the female part of a Luer connector to reduce the stress when said female part is connected to a male part and also to avoid or minimise the disadvantages referred to hereinbefore.

According to the present invention, the female part of a Luer connector is formed with at least one abutment at or adjacent the distal end of the interior of the female part for limiting longitudinal movement of a mating male part within said female part when said male and female parts are interconnected said abutment extending around a portion only of the periphery of said interior.

An embodiment of the invention will now be described, by way of example, reference being made to the Figures of the accompanying diagrammatic drawing in which:

FIG. 1 is a perspective view, partly broken of a barrel portion of a medical stopcock;

FIG. 2 is a side view of the medical stopcock of FIG. 1

FIG. 3 is a longitudinal cross-section on the line A—A of FIG. 2; and

FIG. 4 is a plan cross-section on the line B—B of FIG. 2.

As shown, a barrel 2 forming part of a medical stopcock has a hollow interior. Extending radially outwardly from the outward facing surface of the barrel 2 are three spaced hollow spigots 4, 6 and 8. As is known, spigots 6 and 8 act as inlets and will be connected to a tube through which medical liquid will flow from a source (not shown). The remaining spigot 4 is an outlet spigot which will be connected to a tube for conducting the medical liquid from the stopcock towards a patient or other destination.

The hollow spigots 4, 6 and 8 each communicate with the interior of the barrel 2 and the hollow interior of both inlet spigots 6 and 8 is tapered and dimensioned to comply with the Luer standard for mating with a Luer male part.

According to the present invention at or adjacent the distal end of the interior of each inlet spigot 6, 8 there is formed at least one abutment 10 which will effectively limit the length of engagement between a Luer male part and the interior of the inlet 6, 8. Thus, the male part will be prevented from being forced longitudinally within the female Luer part 6, 8 to produce high tensile stress.

The abutment 10 extends around only a portion of the periphery of the interior and thereby offers very little resistance to the flow of fluid passing through the stopcock. Furthermore, should the free end of a mating male part not engage the abutment 10, then the resulting space between said free end and the abutment 10 would not act as a trap for air and would offer less chance of snagging the free end of a guide-wire. Trapped air is a particular danger in medical applications carrying with it the risk of air emboli. A risk also occurs in pressure monitoring applications since due to the presence of trapped air the user may receive a false reading and may therefore be mislead into reacting incorrectly in critical life threatening situations.

Although as shown in the above described embodiment there are diametrically opposed abutments 10, in an alternative embodiment the abutment could consist of several small ribs which will permit the use of guide wires through the Luer inlets and avoid formation of trapped air as well as negative effects on fluid flowing through the stopcock.

A medical stopcock as described in the above embodiment provides a good flowpath which reduces the risk of the entrapment of air bubbles and "pockets" of drugs and turbulence in the flow of fluid therethrough and makes it possible to use guide-wires with a reduced risk of snagging.

Although reference has been made in the above described embodiment to a medical stopcock clearly the invention applies equally to any rigid or semi-rigid plastic product having a female Luer connector part for interconnection with a mating male Luer connector part.

I claim:

1. A stopcock, comprising:

a main body portion defining an axially extending lumen; and a plurality of hollow spigots extending radially from the main body portion, each spigot having an interior that is in fluid flow communication with the axially extending lumen and each spigot having an inlet spaced from the main body portion and an outlet adjacent to the main body portion wherein the interior of each spigot has a first tapered portion adjacent to the inlet with a first tapered cross-section and a second tapered portion adjacent to the outlet with a second tapered cross-section and at least one of the spigots further includes at least one rib formed in the second tapered portion of the interior of the spigot.

* * * * *